United States Patent
Goitsuka

(10) Patent No.: US 7,226,997 B2
(45) Date of Patent: Jun. 5, 2007

(54) MAST CELL-SPECIFIC SIGNAL TRANSDUCER AND CDNA THEREOF

(75) Inventor: Ryo Goitsuka, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 11/529,217

(22) Filed: Sep. 29, 2006

(65) Prior Publication Data

US 2007/0020732 A1    Jan. 25, 2007

Related U.S. Application Data

(60) Division of application No. 10/717,619, filed on Nov. 21, 2003, now abandoned, which is a continuation-in-part of application No. 09/856,061, filed as application No. PCT/JP00/06351 on Sep. 18, 2000, now Pat. No. 6,831,151.

(30) Foreign Application Priority Data

Sep. 17, 1999    (JP)    ............... 1999-263778

(51) Int. Cl.
*C07K 1/00*    (2006.01)
(52) U.S. Cl. .................... 530/350; 435/69.1
(58) Field of Classification Search .............. None
See application file for complete search history.

(56) References Cited

U.S. PATENT DOCUMENTS 6,831,151 B1    12/2004    Goitsuka

OTHER PUBLICATIONS

Goitsuka et al., *International Immunology*, vol. 12, No. 4, pp. 573-580, 2000.
Goitsuka et al., *Igaku no Ayumi*, vol. 192, No. 10, pp. 1027-1031, 2000.
Cao et al., *J. Exp. Med.*, vol. 190, No. 10, pp. 1527-1534, 1999.
Goitsuka et al., *J. Immunol.*, vol. 161, pp. 5804-5808, 1998.
Jackman et al., *J. Biol. Chem.*, vol. 270, No. 13, pp. 7029-7032, 1995.

*Primary Examiner*—Karen Cochrane Carlson
*Assistant Examiner*—Agnes B. Rooke
(74) *Attorney, Agent, or Firm*—Wenderoth, Lind & Ponack, L.L.P.

(57) ABSTRACT

The present invention provides a signal transducer specifically expressed in mouse mast cells that has the amino acid sequence of SEQ ID No. 2, a signal transducer specifically expressed in human mast cells that has the amino acid sequence of SEQ ID No. 4, polynucleotides encoding these proteins, an expression vector involving these polynucleotides, transformed cells induced by these expression vectors, and antibodies against the foregoing proteins. The signal transducer provided in the present invention is useful for screening of novel medicines against allergic diseases.

2 Claims, 3 Drawing Sheets

MAST CELL-SPECIFIC SIGNAL TRANSDUCER AND CDNA THEREOF

This application is a divisional of Ser. No. 10/717,619, filed Nov. 21, 2003, now abandoned, which is a continuation-in-part application of Ser. No. 09/856,061, filed Jul. 10, 2001, now U.S. Pat. No. 6,831,151, which is a 371 U.S. national stage of International Application No. PCT/JP00/06351, filed Sep. 18, 2000.

TECHNICAL FIELD

The present invention relates to a signal transducer specifically expressed in mouse and human mast cell, and polynucleotides (cDNAs) encoding this protein molecule. More particularly, the present invention relates to a novel protein that is useful, for example, as a target molecule for screening a therapeutic agent for allergic diseases, and various genetic engineering materials useful for production and functional analysis of this protein.

BACKGROUND ART

The type-I allergic response is a complicated immune reaction induced by release of granules containing histamine and serotonin through cross-linking of high affinity IgE receptors mainly expressed in the mast cell and basophilic leukocytes with IgE antibodies and allergens. This reaction has been elucidated to be composed of the following three stages:
A) An initial stage including production of cytokines such as IL-4 and IL-5 from T cell by stimulation of allergens, production of the IgE antibody from B cell, and differentiation and proliferation of the mast cells induced by production of the cytokines;
B) An intermediate stage from cross-linking of Fcε receptors by the IgE antibody and allergen to degranulation of the mast cell; and
C) A later stage such as enhanced vascular permeability by histamine and serotonin after degranulation.

The inventors of the present invention have isolated an adapter molecule BASH that is specifically expressed in B cell (J. Immunol., 161:5804–5808, 1998). This BASH has a similar molecular structure to SLP-76 (J. Biol. Chem., 270:7029–7032, 1995) that is expressed in T cell, and indicates the presence of a family of signal transducers specific to hemopoietic immunoreceptors through structural and functional analysis.

While suppression of IgE antibody production (Primary Stage) by B cell using a hyposentitization therapy, or suppression of the later stage by administration of anti-histaminic agent have been used today for treating allergies, neither of them serves as an effective therapy in the current situations.

A part of the molecular mechanism of the type-I allergy response is being made clear, on the other hand, as described above. However, the signal transduction mechanism involved in degranulation of mast cell through the high affinity IgE receptor has not been known yet. It is inevitable to elucidate the molecule involved in the degranulation process of mast cell not only for elucidating the molecular mechanism of the allergy response but also for developing therapeutic methods or therapeutic agents of the allergic diseases. Particularly, since the mast cell plays a critical role in expression of the allergic conditions, the signal transducer that is specifically expressed in mast cell is quite important for developing novel antiallergic agents that selectively block the Fcε receptor signal transduction system that causes the degranulation reaction involving release of histamine and serotonin.

The object of the present invention performed based on the foregoing situations is to provide signal transducers specifically expressed in mouse and human mast cells, and polynucleotides (cDNAs) encoding these protein molecules.

Another object of the present invention is to provide various genetic engineering materials involved in the signal transducers.

DISCLOSURE OF INVENTION

For solving the problems above, the present invention provides the following inventions (1) to (10).
(1) A signal transducer specifically expressed in mouse mast cells, which is a purified protein having the amino acid sequence of SEQ ID NO: 2.
(2) A signal transducer specifically expressed in human mast cells, which is a purified protein having the amino acid sequence of SEQ ID NO: 4.
(3) A polynucleotide consisting of the base sequence of SEQ ID NO:1, which encodes the protein of (1).
(4) A polynucleotide having the base sequence of SEQ ID NO:3, which encodes the protein of (4).
(5) An expression vector involving the polynucleotide of (3).
(6) An expression vector involving the polynucleotide of (4).
(7) A cell transformed with the expression vector of (5), which produces the protein of (6).
(8) A cell transformed with the expression vector of (6), which produces the protein of (2).
(9) An antibody against the protein of (1).
(10) An antibody against the protein of (2).

BEST MODE FOR CARRYING OUT THE INVENTION

Figure 1:
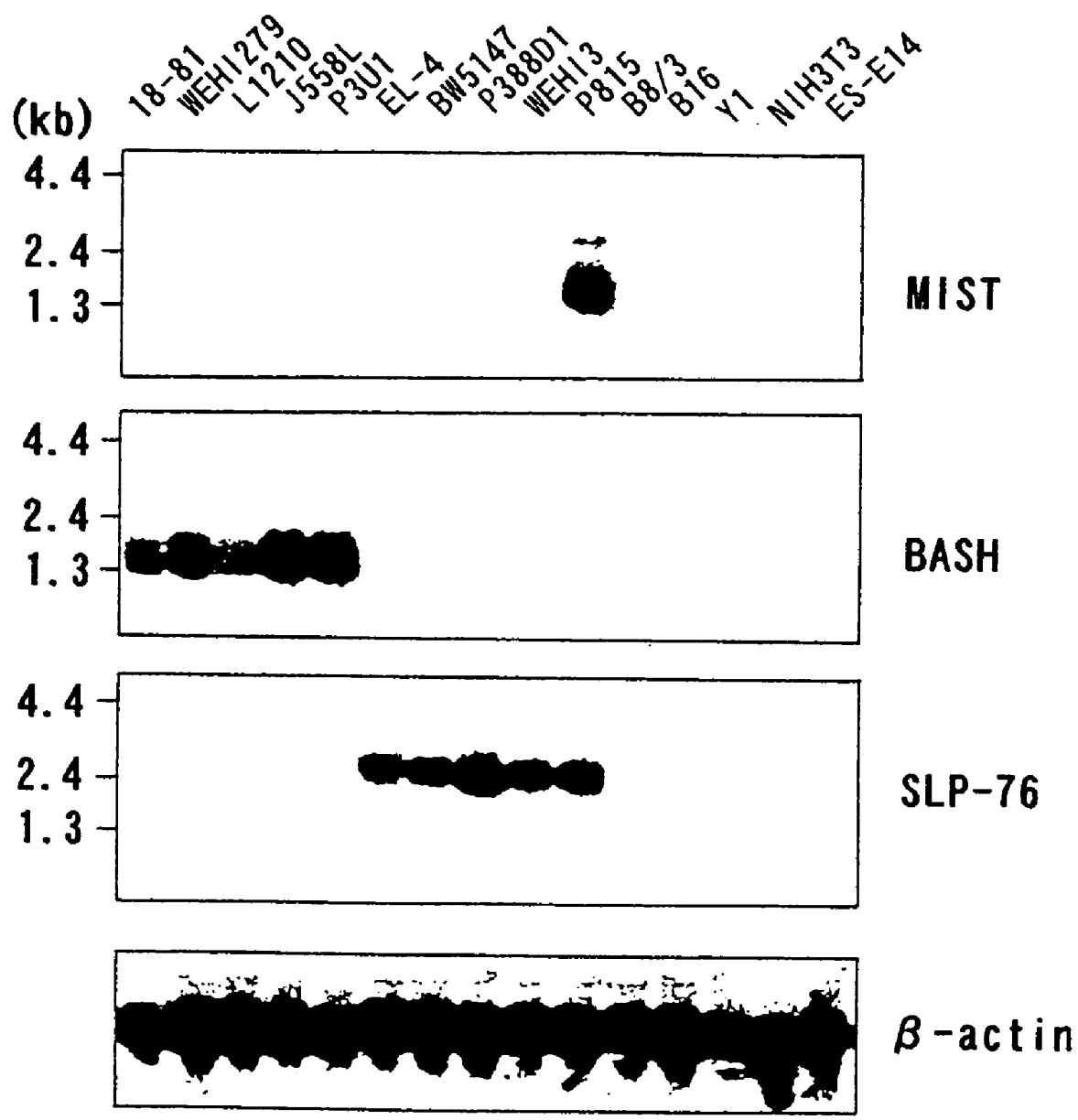
FIG. 1 shows the results of Northern blot analysis investigating expression of MIST, BASH and SLP-76 in the hemopoietic and non-hemopoietic cell lines. 18-18: B-precursor cells, WEHI1279: B cells, L1210: B-lymphocyte precursor cells, J558L and P3U1: plasma cells, EL-4 and BW5147: T cells, P388D1 and WEHI3: macrophages, P815: mast cell, B8/3: erythroblast, and B16,Y1, NIH3T3 and ES-E14: non-hemopoirtic cell lines.

By screening the expression sequence tag (EST) database, the present inventor identified an EST clone from 13.5 day mouse embryo cDNA library (GenBank accession No. AA166259) which showed a significant amino acid homology to the SH2 domain of chicken BASH (J. Immunol. 161:5804–5808, 1998). The inventor further found that the 1.8 kb mRNA of this clone is not expressed in other hemopoietic cell lines and non-hemopoietic cell lines (such as B cell, T cell and macrophages) in which BASH and SLP-76 are expressed, and is expressed only in mastcytoma cell line P815 (FIG. 1). The expressed protein molecule was named as MIST (Mast Cell-specific Immunoreceptor Signal Transducer) form such specific expression pattern and its function to be described hereinafter.

Embodiments of the present invention will be described in detail hereinafter.

The MISTs according to the inventions (1) and (2) are proteins that are specifically expressed in mouse and human mast cells. The mouse MIST in the invention (1) is a protein encoded in the polynucleotide (full-length cDNA: SEQ ID NO:1) of the invention (3). The human MIST in the invention (2) is, on the other hand, a protein encoded in the polynucleotide (full-length cDNA: SEQ ID NO:3) of the invention (4).

While the mouse MIST in the invention (1) and human MIST in the invention (2) may be obtained by a method for isolating from organs and cell lines of mouse and human, respectively, by a method for preparing a peptide by a chemical synthesis based on the amino acid sequences provided by the present invention, or by a production method using a recombinant DNA technology using the polynucleotides of the inventions (3) and (4), the recombinant DNA method is preferably used. For example, RNA is prepared by in vitro transcription from a vector having the polynucleotides of the inventions (3) and (4), and MIST is expressed in vitro by in vitro translation using the RNA as a template. The mouse MIST and human MIST encoded by the polynucleotide can be expressed in large scale in prokaryotic cells such as E. coli and Bacillus subtilis, and in eukaryotic cells such as yeast, insect cells, mammal cells and plant cells by recombination of the coding region with the expression vector using a conventional method.

The polynucleotide (SEQ ID NO:1) of the invention (3) can be obtained by a chemical synthesis or screening of the mouse cDNA library. For cloning the desired polynucleotide from a cDNA library, an oligonucleotide is synthesized based on the base sequence in an arbitrary portion of SEQ ID NO:1, and the polynucleotide is screened by colony or plaque hybridization by the method known in the art using the oligonucleotide as a probe. Alternatively, oligonucleotides that can hybridize to both ends of the desired polynucleotide are synthesized, and the polynucleotide of the invention (3) is prepared by a PCR method using the oligonucleotides as primers and genomic DNA isolated from the mouse cells as a template.

The polynucleotide (SEQ ID NO:3) of the invention (4) also can be obtained by the same manner as SEQ ID No. 1 using human cDNa library etc.

For producing the MIST by expressing the polynucleotide in vitro translation, for example, the polynucleotide of the invention (3) or (4) is recombined into a vector having a RNA polymerase promoter [the inventions (5) and (6)], and the recombinant vector is added to an in vitro translation system such as a lysate of rabbit reticulocytes or wheat germ extract containing the RNA polymerase corresponding to the promoter, thereby producing the mouse and human MIST in vitro. Examples of the RNA polymerase promoters include T7, T3 and SP6. Examples of the vectors containing the RNA polymerase are pKA1, pCDM8, pT3/T7 18, pT7/3 19 and pBluescript II.

For producing the MIST by expressing the polynucleotide in microorganisms such as E. coli, an expression vector [the invention (5) and (6)] is prepared by recombining the polynucleotide of the invention (3) or (4) into an expression vector having an origin capable of replication in microorganisms, a promoter, a ribosome binding site, DNA cloning sites and terminator. After transforming host cell with this expression vector, the transformant obtained [the inventions (7) and (8)] is cultured for large scale production of MIST encoded by these polynucleotides in microorganisms. MIST fragments containing arbitrary regions may be obtained by adding an initiation codon and a termination codon before and after the arbitrary coding region. Or, the protein can be expressed as a fusion protein with other proteins. Only the protein regions encoded by this cDNA may be obtained by cleaving the fusion protein with an appropriate protease. Examples of the expression vector for use in E. coli include a pUC series vector, pBluescript II, pET expression system and pGEX expression system.

For producing the MIST by expressing the polynucleotide in eukaryotic cell, the polynucleotide of the invention (3) or (4) is recombined with an expression vector for eukaryotic cells that comprises a promoter, splicing site, poly(A) additional site to prepare a recombinamt vector [the inventions (5) and (6)], and the vector is introduced into the eukaryotic cell to transform a host cell [the inventions (7) and (8)]. Examples of the expression vectors include pKA1, pCDM8, pSVK3, pMSG, pSVL, pBK-CMV, pBK-RSV, EBV vector, pRS and pYES2. MIST may be expressed as a fusion protein to which various tags such as His tag, FLAG tag and GFP by using pIND/V5-His, pFLAG-CMV-2, pEGFP-N1 and pEGFP-C1 as an expression vector. While cultured cells of a mammal such as monkey kidney cells COS7 and Chinese hamster ovary cells CHO, budding yeast, dividing yeast, silkworm cells and African clawed frog egg cells are usually used as the eukaryotic cells, any eukaryotic cells may be used so long as they are able to express MIST. The expression vector can be introduced into the eukaryotic cell by a conventional method such as an electroporation method, a calcium phosphate method, a liposome method, and a DEAE dextran method.

A combination of separation methods known in the art may be used for purifying the desired protein from the culture after allowing MIST to express in the prokaryotic cells and eukaryotic cells. For example, these methods include treatment with a denaturation reagent such as urea or with a surface active agent, ultrasonic treatment, enzymatic digestion, salting-out and solvent precipitation method, dialysis, centrifugation, ultrafiltration, gel filtration, SDS-PAGE, isoelectric focusing electrophoresis, ion exchange chromatography, hydrophobic chromatography, affinity chromatography and reversed phase chromatography.

The mouse MIST of the invention (1) and the human MIST of the invention (2) contain any peptide fragments (five amino acid residues or more) represented by SEQ ID NOs: 2 and 4. These peptide fragments may be used for preparing antibodies. The MISTs of the inventions (1) and (2) are modified in any ways in the cell after translation. Accordingly, these modified proteins are also included within the scope of the present invention. Examples of modification after translation include elimination of N-terminal methionine, N-terminal acetylation, addition of sugar chains, restricted degradation by an intracellular protease, addition of miristoleic acid, isoprenylation and phosphorylation.

Polymorphism by individual differences is often observed in the animal gene. Accordingly, polynucleotides having addition or deletion of one or plural nucleotides and/or substitution with other nucleotides in the base sequence of SEQ ID NOs: 1 and 3 are also included within the scope of the present invention.

Likewise, MISTs having addition or deletion of one or plural amino acids and/or substitution with other amino acids caused by the alteration of polynucleotides as described above are also included within the scope of the present invention so long as it has an activity of the MIST containing the amino acid sequences of SEQ ID NOs: 2 and 4.

The polynucleotides in the inventions (3) and (4) also include DNA fragments (10 bp or more) comprising any partial base sequence of SEQ ID NOs: 1 and 3. DNA fragments comprising sense strand and antisense strans are also included within the scope as described above.

The antibodies according to the inventions (9) and (10) can be obtained from serums of an animals immunized with the proteins of the inventions (1) and (2). Chemically synthesized peptides based on the amino acid sequences of SEQ ID NOs: 2 and 4, and MIST itself expressed in the eukaryotic or prokaryotic cells may be used for the antigen. Otherwise, the antibodies may be produced from collected serums after introducing the expression vector for the eukaryotic cell into the muscle or skin of an animal by injection or using a gene gun (for example, the method described in Japanese Patent Publication No. 7-31387). The animals used include mouse, rat, rabbit, goat and chicken. Monoclonal antibodies against MIST can be obtained by preparing a hybridoma by fusing B cell extracted from an immunized animal with myeloma cells.

EXAMPLES

The present invention is described in more detail with Examples, the present invention is not restricted in any sense by the Examples as set forth below.

Example 1 cDNA Cloning

Full-length mouse MIST cDNA was isolated from PT18 cDNA library with 5'- and 3'-RACE (Marathon cDNA amplification kit, made by Clontech Co.), using primers prepared based on the sequence information of EST clone (GenGank accession No. AA166259). The partial cDNA of human MIST was amplified by PCR using mRNA prepared from human cord blood mast cell (HCMC) cultured with IL-6 and the stem cell factor (SFC: Peprotech) according to the method in "Blood 86:3705–3714, 1995.

The sequence of the cDNA obtained was determined by the method known in the art, confirming that the mouse MIST cDNA comprises the base sequence represented by SEQ ID NO:1 and the human MIST partial cDNA comprises the base sequence represented by SEQ ID NO:3. It was also confirmed that the mouse MIST has the amino acid sequence represented by SEQ ID NO:2 with a molecular weight of about 60 kDa. Eight Tyr residues capable of phosphorylation are found in the mouse MIST from the N-terminus to the central part. The C-terminal part contains an SH2 domain which is most similar to the SH2 domain of mouse BASH and SLP-76 in amino acid level (41% and 53% identities, respectively). In addition, the central part of MIST is rich in Pro residues, and contains SH3 domain-binding motif. Consequently, MIST was confirmed to have the features as a signal molecule.

The human MIST showed, on the other hand, 60% homology with the mouse MIST in the amino acid level.

Example 2

Construction of Expression Vector

The coding region of the mouse MIST cDNA obtained in Example 1 was amplified by PCR, and the amplified region was inserted between the EcoRI and Sal I sites of pCATneo expression vector (J. Immunol., 161:5804–5808, 1998) to construct a recombinant expression vector (pCATneo-MIST-WT).

The MIST mutant (MIST-YF) in which amino acids (Tyr) at 69, 96, 101, 153, 174 and 188 in SEQ ID NO:2 were substituted with other amino acids (Phe) was prepared by a PCR-based mutagenesis using a commercially available mutation kit (made by Stratagene Co.), and subcloned the MIST-YF into the pCATneo to construct a recombinant expression vector (pCATneo-MIST-YF).

Example 3

Preparation of Transformed Cells

The rat must cell line RBL-2H3 were transfected with the recombinant expression vectors pCATneo-MIST or pCATneo-MIST-YF prepared in Example 2 to prepare the transformed cell RBL-2H3-MIST and RBL-2H3-MIST-YE.

Example 4

Preparation of Antibody

An anti-MIST antibody was prepared from a rabbit immunized with a fusion protein of a polypeptide comprising the amino acid sequence 193–435 in SEQ ID NO: 2 and glutathione-5-transferase (GST). The antisera were at first precleared with Seharose beads coupled with GST alone, and then purified with an affinity column coupled with GST-MIST fusion protein. Specificity of the antibody purified with affinity chromatography was confirmed by an immunoblot analysis on cell lysates from COS cells transfected with mouse MIST cDNA.

Example 5

Confirmation of MIST Expression in Various Cell Lines

Expression of the mouse and human MISTs obtained in Example 1 was confirmed by RT-PCR. The objective cells were IL-3-induced mouse bone marrow-derived mast cells (BMMC), mouse mast cell line PT18, human mast cells (HCNC) cultured with SCF and IL-6, and other hemocyte cell lines (Jurkat: human T cell, Romas: human B cell, KU812: human basophil precursor cell, EOL-1: human eosinophil precursor cell).

Figure 2:
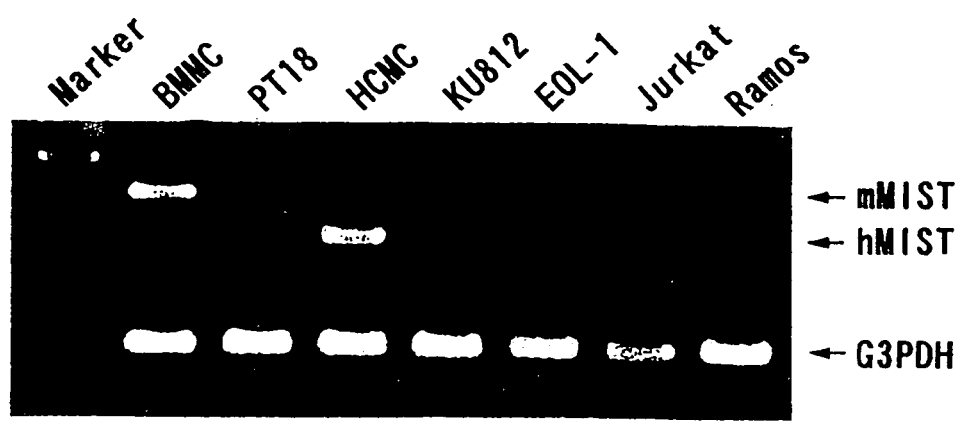
FIG. 2 shows the results of RT-PCR analysis investigating expression of MIST in various hemopoietic cell lines.

The results are as shown in FIG. 2. Although expression of MIST was found in mast cells BMMC, PT18 and HCNC, other cell lines showed no expression.

Figure 3:
FIGS. 3 and 4 show the results of immunohistological analysis investigating expression of MIST in inflammatory mast cell in atopic dermatitis of the NC/Nga mouse.
Figure 4:

By using the anti-MIST antibody prepared in Example 4, serial tissue sections of NC/Nga mice, which spontaneously develop atopic dermatitis (J. Imunol., 9:461–466, 1997) were stained to clarify whether MIST protein is expressed in normal mast cells in in vivo. The results are shown in FIGS. 3 and 4. Expression of MIST was observed in the inflammatory mast cells in the mouse.

It was confirmed from the results as described above that MIST is a protein specifically expressed in mast cell.

Example 6

Confirmation of Phosphorylation of Tyrosine in MIST

Phosphorylation of tyrosine in MIST by stimulating with FcεRI was investigated using the rat mast cell line RBL-2H3 in which signal transduction of FcεRI had been confirmed.

The transformed cell RBL-2H3-MIST prepared in Example 3 was cultured with 10 μg of anti-DNP mouse IgE (made by Sigma Co.) for 1 hour, and the cells were stimulated with 100 ng/ml of DNP-HSA. The cells were lysed with 1% NP40 lysis buffer, and the lysate was subjected to immune precipitation together with various antibodies.

Tyrosine of the MIST molecule was phosphorylated by stimulating the Fcε receptor on the mast cell IgE and antigens, and MIST associate with signal molecules such as PLC-γ and Vav. Consequently, the MIST molecule was confirmed to be a signal molecule existing at the downstream of the Fcε receptor. MIST was evidently phosphorylated by Lyn kinase among tyrosine kinases present in the mast cell, showing that the Lyn kinase has an important role for degranulation of the mast cell.

Example 7

Investigation of MIST Function in Degranulation of Mast Cell

The effect of over expression of MIST and mutation type MIST on degranulation of the cells was investigated using the transformed cells RBL-2H3-MIST and RBL-2H3-MIST-YF prepared in Example 3.

The cells were cultured with 1 μg/ml of anti-DNP mouse IgE overnight, washed twice with PBS, and stimulated with DNP-HSA at 37° C. for 30 minutes. Degranulation was confirmed by measuring release of β-hexosaminidase by the method described in the literature (Int. Immunol., 7:251–258, 1992).

Figure 5:
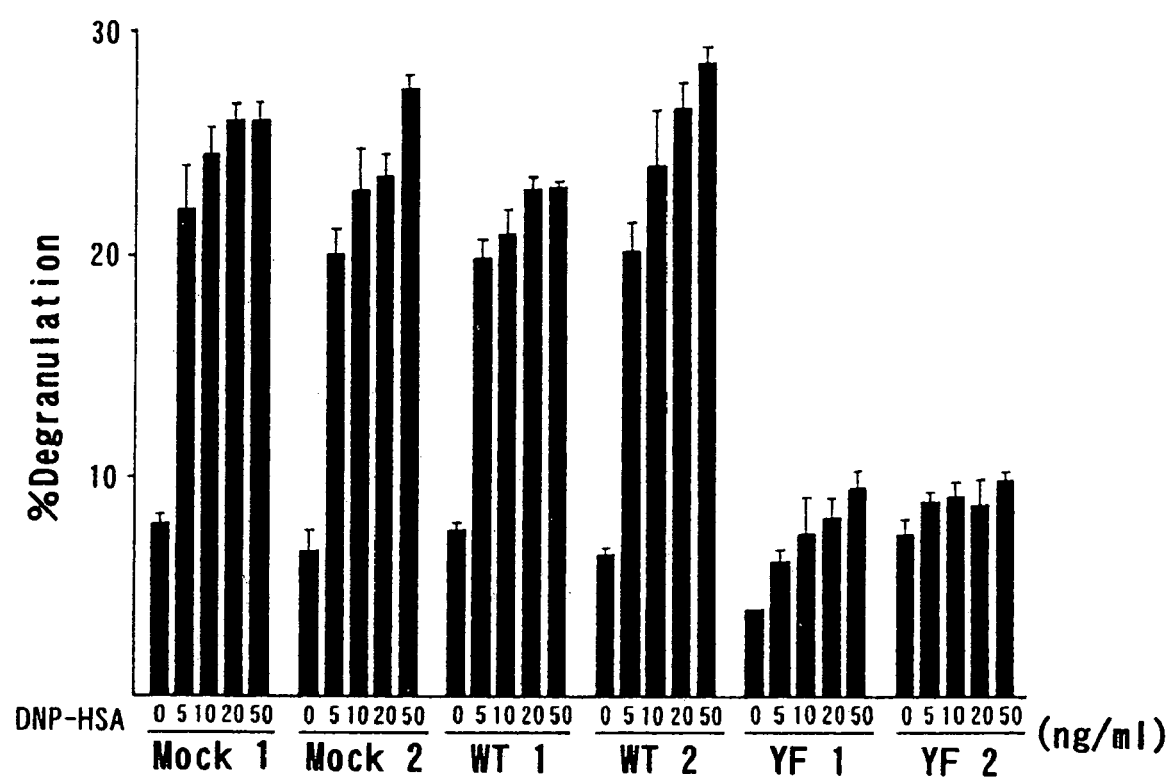
FIG. 5 shows the results of degranulation reaction of RBL-2H3 clone expressing wild-type or mutant MIST.

The results are shown in FIG. 5. Although degranulation of the mast cell was not affected by stimulation with the Fcε receptor when a wild type MIST was over expressed, degranulation of the mast cell via the FCε receptor was significantly suppressed by over expression of the MIST mutant (MIST-YF).

It was confirmed from the results above that the MIST molecule plays an important role in the signal transduction pathway from stimulation by the Fcε receptor through degranulation.

INDUSTRIAL APPLICABILITY

The present invention provides signal transducers that are specifically expressed in mouse and human mast cells, polynucleotides (cDNAs) encoding this protein molecule and various gene engineering materials concerning these signal transducers. Screening of novel agents for allergic diseases becomes possible by using these signal transducers as targets.

The invention claimed is:

1. A signal transducer specifically expressed in human mast cells, which is a purified protein having the amino acid sequence of SEQ ID NO:4.

2. A signal transducer specifically expressed in human mast cells, which is a purified protein encoded by the nucleic acid sequence of SEQ ID NO:3.

* * * * *

SEQUENCE LISTING

```
<160> NUMBER OF SEQ ID NOS: 4

<210> SEQ ID NO 1
<211> LENGTH: 1721
<212> TYPE: DNA
<213> ORGANISM: Mus musculus
<220> FEATURE:
<221> NAME/KEY: CDS
<222> LOCATION: (255)..(1562)
<300> PUBLICATION INFORMATION:
<301> AUTHORS: Goitsuka R., et al.
<302> TITLE: A BASH/SLP-76-related adaptor protein MIST/Clink involved
      in IgE receptor-mediated mast cell degranuation
<303> JOURNAL: Int. Immunol.
<304> VOLUME: 12
<305> ISSUE: 4
<306> PAGES: 573-580
<307> DATE: 2000
<308> DATABASE ACCESSION NUMBER: GenBank/AB021220
<309> DATABASE ENTRY DATE: 2000-05-26

<400> SEQUENCE: 1
acgaggccaa actgcccagg tctgtggctg cgtttctcgg aaaaccaaaa ctcaacaggc      60
acatacaagg cactctctgc tgaaggactc tgctgagggg agagaacatg tcaactctat     120
cttacagagt gctccaggat gcgaccgtgg accccctttc caggagctag ccgtctcaac     180
actgagccct tgactaaagg aagactgagc aggctgagtt gaagatccct ctcttttgcc     240
aggtgccaag gacc atg acc agc cag ggc aat aaa agg aca acg aaa gaa      290
             Met Thr Ser Gln Gly Asn Lys Arg Thr Thr Lys Glu
               1               5                  10 gga ttc ggt gat ctg aga ttc cag aac gtc tct ctg ctg aaa aat agg      338
Gly Phe Gly Asp Leu Arg Phe Gln Asn Val Ser Leu Leu Lys Asn Arg
         15                  20                  25 tca tgg cca agc ctc agc agt gcc aaa ggg cgg tgt cga gcg gtt ctg      386
Ser Trp Pro Ser Leu Ser Ser Ala Lys Gly Arg Cys Arg Ala Val Leu
     30                  35                  40
```

```
gaa cca ctt ccg gat cac aga agg aac ttg gct ggg gtc cca ggt gga        434
Glu Pro Leu Pro Asp His Arg Arg Asn Leu Ala Gly Val Pro Gly Gly
 45              50                  55                  60 gaa aaa tgc aac agt aac aac gac tac gaa gat cct gag ttc cag ctg        482
Glu Lys Cys Asn Ser Asn Asn Asp Tyr Glu Asp Pro Glu Phe Gln Leu
                 65                  70                  75 ctg aag gca tgg cca tca atg aaa att tta cca gcc aga cct atc cag        530
Leu Lys Ala Trp Pro Ser Met Lys Ile Leu Pro Ala Arg Pro Ile Gln
             80                  85                  90 gaa tcg gaa tac gca gat aca cgc tat ttc cag gat atg atg gag gct        578
Glu Ser Glu Tyr Ala Asp Thr Arg Tyr Phe Gln Asp Met Met Glu Ala
         95                 100                 105 ccc ctt ctg tta cct ccc aag gct tct gtc tcc act gag aga caa acc        626
Pro Leu Leu Leu Pro Pro Lys Ala Ser Val Ser Thr Glu Arg Gln Thr
    110                 115                 120 agg gat gtg agg atg aca cag ctg gaa gaa gtg gac aag cct acc ttc        674
Arg Asp Val Arg Met Thr Gln Leu Glu Glu Val Asp Lys Pro Thr Phe
125                 130                 135                 140 aag gat gtc aga agc caa cgc ttt aaa gga ttc aaa tac aca aaa ata        722
Lys Asp Val Arg Ser Gln Arg Phe Lys Gly Phe Lys Tyr Thr Lys Ile
                145                 150                 155 aac aag act cct ttg cca cct cct cgg cct gct atc act ctc ccc aag        770
Asn Lys Thr Pro Leu Pro Pro Pro Arg Pro Ala Ile Thr Leu Pro Lys
            160                 165                 170 aag tac caa ccc tta ccc cca gca cca cca gag gag agc agt gca tac        818
Lys Tyr Gln Pro Leu Pro Pro Ala Pro Pro Glu Glu Ser Ser Ala Tyr
        175                 180                 185 ttc gct cca aag ccc acc ttt cca gaa gtc cag agg ggg ccc agg cag        866
Phe Ala Pro Lys Pro Thr Phe Pro Glu Val Gln Arg Gly Pro Arg Gln
    190                 195                 200 agg agt gca aaa gac ttc agt agg gtc ctt gga gca gaa gaa gaa tct        914
Arg Ser Ala Lys Asp Phe Ser Arg Val Leu Gly Ala Glu Glu Glu Ser
205                 210                 215                 220 cac cac cag aca aag cca gaa tct tct tgc cca tca tca aac caa aac        962
His His Gln Thr Lys Pro Glu Ser Ser Cys Pro Ser Ser Asn Gln Asn
                225                 230                 235 aca cag aag agt cca cct gcc att gcc agc tct tcc tac atg cca gga       1010
Thr Gln Lys Ser Pro Pro Ala Ile Ala Ser Ser Ser Tyr Met Pro Gly
            240                 245                 250 aag cac agt ata caa gcc aga gac cat aca ggt agc atg cag cac tgt       1058
Lys His Ser Ile Gln Ala Arg Asp His Thr Gly Ser Met Gln His Cys
        255                 260                 265 cct gct cag aga tgc caa gct gca gcc agc cac agc cct cga atg ctg       1106
Pro Ala Gln Arg Cys Gln Ala Ala Ala Ser His Ser Pro Arg Met Leu
    270                 275                 280 ccc tat gaa aac aca aac tcg gag aaa cct gac ccc aca aag cct gat       1154
Pro Tyr Glu Asn Thr Asn Ser Glu Lys Pro Asp Pro Thr Lys Pro Asp
285                 290                 295                 300 gag aag gat gtc tgg cag aat gaa tgg tac att gga gaa tac agt cgc       1202
Glu Lys Asp Val Trp Gln Asn Glu Trp Tyr Ile Gly Glu Tyr Ser Arg
                305                 310                 315 cag gca gtg gaa gat gtg tta atg aaa gag aac aag gat ggt act ttt       1250
Gln Ala Val Glu Asp Val Leu Met Lys Glu Asn Lys Asp Gly Thr Phe
            320                 325                 330 ttg gtc cga gac tgc tct aca aaa tcc aag gca gaa cca tat gtt ttg       1298
Leu Val Arg Asp Cys Ser Thr Lys Ser Lys Ala Glu Pro Tyr Val Leu
        335                 340                 345 gtg gtg ttt tat ggg aac aag gtc tac aat gtg aaa atc cgt ttc ctc       1346
Val Val Phe Tyr Gly Asn Lys Val Tyr Asn Val Lys Ile Arg Phe Leu
```

-continued

|  |  |  |  |  |  |  |  |  |  |  |  |  |  |  |  |
|---|---|---|---|---|---|---|---|---|---|---|---|---|---|---|---|
|  | 350 |  |  |  | 355 |  |  |  |  | 360 |  |  |  |  |  |
| gag | agc | aat | caa | cag | ttt | gcc | ctg | ggc | aca | gga | cta | cga | gga | aat | gag | 1394 |
| Glu | Ser | Asn | Gln | Gln | Phe | Ala | Leu | Gly | Thr | Gly | Leu | Arg | Gly | Asn | Glu |  |
| 365 |  |  |  |  | 370 |  |  |  |  | 375 |  |  |  |  | 380 |  |
| atg | ttt | gat | tct | gtg | gaa | gac | atc | att | gaa | cac | tac | aca | tat | ttt | ccc | 1442 |
| Met | Phe | Asp | Ser | Val | Glu | Asp | Ile | Ile | Glu | His | Tyr | Thr | Tyr | Phe | Pro |  |
|  |  |  |  | 385 |  |  |  |  | 390 |  |  |  |  | 395 |  |  |
| att | ctg | cta | ata | gat | ggg | aaa | gac | aag | gct | gca | cgc | agg | aaa | cag | tgc | 1490 |
| Ile | Leu | Leu | Ile | Asp | Gly | Lys | Asp | Lys | Ala | Ala | Arg | Arg | Lys | Gln | Cys |  |
|  |  |  | 400 |  |  |  |  | 405 |  |  |  |  | 410 |  |  |  |
| tac | ctc | acc | cag | cca | ctg | cct | ctc | gcc | agg | ctc | ctt | ctc | act | cag | tac | 1538 |
| Tyr | Leu | Thr | Gln | Pro | Leu | Pro | Leu | Ala | Arg | Leu | Leu | Leu | Thr | Gln | Tyr |  |
|  |  | 415 |  |  |  |  | 420 |  |  |  |  | 425 |  |  |  |  |
| tcc | agc | cag | gca | ctt | cat | gag | taa | gaagcccagc cagatatccc cgcatcagtg |  |  |  |  |  |  |  | 1592 |
| Ser | Ser | Gln | Ala | Leu | His | Glu |  |  |  |  |  |  |  |  |  |  |
|  | 430 |  |  |  | 435 |  |  |  |  |  |  |  |  |  |  |  | gcctgggcct tgtctcattc ctggctcaat ggattcagtt cttcttccat ctgcatttat     1652 ctgcaaagta ttattttctg tgtcttcaag ggatgatttt ttgactctgt aaaaaaaaaa     1712 aaaaaaaaa                                                             1721

<210> SEQ ID NO 2
<211> LENGTH: 435
<212> TYPE: PRT
<213> ORGANISM: Mus musculus

<400> SEQUENCE: 2

Met Thr Ser Gln Gly Asn Lys Arg Thr Thr Lys Glu Gly Phe Gly Asp
 1               5                  10                  15

Leu Arg Phe Gln Asn Val Ser Leu Leu Lys Asn Arg Ser Trp Pro Ser
                20                  25                  30

Leu Ser Ser Ala Lys Gly Arg Cys Arg Ala Val Leu Glu Pro Leu Pro
            35                  40                  45

Asp His Arg Arg Asn Leu Ala Gly Val Pro Gly Gly Glu Lys Cys Asn
        50                  55                  60

Ser Asn Asn Asp Tyr Glu Asp Pro Glu Phe Gln Leu Leu Lys Ala Trp
 65                  70                  75                  80

Pro Ser Met Lys Ile Leu Pro Ala Arg Pro Ile Gln Glu Ser Glu Tyr
                85                  90                  95

Ala Asp Thr Arg Tyr Phe Gln Asp Met Met Glu Ala Pro Leu Leu Leu
            100                 105                 110

Pro Pro Lys Ala Ser Val Ser Thr Glu Arg Gln Thr Arg Asp Val Arg
        115                 120                 125

Met Thr Gln Leu Glu Glu Val Asp Lys Pro Thr Phe Lys Asp Val Arg
    130                 135                 140

Ser Gln Arg Phe Lys Gly Phe Lys Tyr Thr Lys Ile Asn Lys Thr Pro
145                 150                 155                 160

Leu Pro Pro Pro Arg Pro Ala Ile Thr Leu Pro Lys Lys Tyr Gln Pro
                165                 170                 175

Leu Pro Pro Ala Pro Pro Glu Glu Ser Ser Ala Tyr Phe Ala Pro Lys
            180                 185                 190

Pro Thr Phe Pro Glu Val Gln Arg Gly Pro Arg Gln Arg Ser Ala Lys
        195                 200                 205

Asp Phe Ser Arg Val Leu Gly Ala Glu Glu Ser His His Gln Thr
    210                 215                 220

Lys Pro Glu Ser Ser Cys Pro Ser Ser Asn Gln Asn Thr Gln Lys Ser

-continued

```
                225                 230                 235                 240

Pro Pro Ala Ile Ala Ser Ser Tyr Met Pro Gly Lys His Ser Ile
                245                 250                 255

Gln Ala Arg Asp His Thr Gly Ser Met Gln His Cys Pro Ala Gln Arg
            260                 265                 270

Cys Gln Ala Ala Ala Ser His Ser Pro Arg Met Leu Pro Tyr Glu Asn
            275                 280                 285

Thr Asn Ser Glu Lys Pro Asp Pro Thr Lys Pro Asp Glu Lys Asp Val
        290                 295                 300

Trp Gln Asn Glu Trp Tyr Ile Gly Glu Tyr Ser Arg Gln Ala Val Glu
305                 310                 315                 320

Asp Val Leu Met Lys Glu Asn Lys Asp Gly Thr Phe Leu Val Arg Asp
                325                 330                 335

Cys Ser Thr Lys Ser Lys Ala Glu Pro Tyr Val Leu Val Phe Tyr
                340                 345                 350

Gly Asn Lys Val Tyr Asn Val Lys Ile Arg Phe Leu Glu Ser Asn Gln
                355                 360                 365

Gln Phe Ala Leu Gly Thr Gly Leu Arg Gly Asn Glu Met Phe Asp Ser
        370                 375                 380

Val Glu Asp Ile Ile Glu His Tyr Thr Tyr Phe Pro Ile Leu Leu Ile
385                 390                 395                 400

Asp Gly Lys Asp Lys Ala Ala Arg Arg Lys Gln Cys Tyr Leu Thr Gln
                405                 410                 415

Pro Leu Pro Leu Ala Arg Leu Leu Leu Thr Gln Tyr Ser Ser Gln Ala
                420                 425                 430

Leu His Glu
        435

<210> SEQ ID NO 3
<211> LENGTH: 1814
<212> TYPE: DNA
<213> ORGANISM: Homo sapiens
<220> FEATURE:
<221> NAME/KEY: CDS
<222> LOCATION: (241)..(1527)
<300> PUBLICATION INFORMATION:
<308> DATABASE ACCESSION NUMBER: GenBank/AB110420
<309> DATABASE ENTRY DATE: 2003-05-22
<313> RELEVANT RESIDUES: (1)..(1814)

<400> SEQUENCE: 3
ggctgcattt cacaggaaac caagtctaaa acggacctat caggaggttt tctgctgaag      60
ggcactgctt agcatcgaga agaattcaac ccaccgcctt actaatttcc agtgccccaa     120
ggtctctgca ctgccgcccc tcctcacagg agacggacac ctcagcctag atcccttggt     180
gctctccacg ctgttcaggc tgaattgaag agccctctta cccgccaggt gccaagaact     240 atg aac agg cag ggc aat aga aag aca act aaa gaa gga tcc aac gat     288
Met Asn Arg Gln Gly Asn Arg Lys Thr Thr Lys Glu Gly Ser Asn Asp
1               5                  10                  15 ttg aaa ttc cag aac ttc agt ctg cca aaa aac agg tca tgg cct cgc     336
Leu Lys Phe Gln Asn Phe Ser Leu Pro Lys Asn Arg Ser Trp Pro Arg
            20                  25                  30 atc aat agt gcc aca ggc cag tac cag agg atg aac aag cct ctt cta     384
Ile Asn Ser Ala Thr Gly Gln Tyr Gln Arg Met Asn Lys Pro Leu Leu
        35                  40                  45 gac tgg gaa aga aac ttt gct gca gtc ctg gat gga gca aaa ggc cac     432
Asp Trp Glu Arg Asn Phe Ala Ala Val Leu Asp Gly Ala Lys Gly His
    50                  55                  60
```

-continued

| | | |
|---|---|---|
| agt gat gat gac tat gat gac cct gag ctt cgg atg gaa gag aca tgg<br>Ser Asp Asp Asp Tyr Asp Asp Pro Glu Leu Arg Met Glu Glu Thr Trp<br>65                    70                    75                    80 | 480 |
| cag tcg att aaa att tta cca gcc cgg cct ata aag gaa tct gaa tat<br>Gln Ser Ile Lys Ile Leu Pro Ala Arg Pro Ile Lys Glu Ser Glu Tyr<br>                    85                    90                    95 | 528 |
| gca gat aca cac tat ttc aag gtt gca atg gac act ccc ctt ccg tta<br>Ala Asp Thr His Tyr Phe Lys Val Ala Met Asp Thr Pro Leu Pro Leu<br>                    100                   105                  110 | 576 |
| gac acc agg acc tct atc tcc att gga cag ccg acc tgg aac aca cag<br>Asp Thr Arg Thr Ser Ile Ser Ile Gly Gln Pro Thr Trp Asn Thr Gln<br>          115                   120                   125 | 624 |
| acg agg ttg gaa aga gtg gac aaa ccc att tcc agg gac gtc aga agc<br>Thr Arg Leu Glu Arg Val Asp Lys Pro Ile Ser Arg Asp Val Arg Ser<br>130                    135                   140 | 672 |
| caa aac att aaa gga gat gca tcc gta aga aag aac aag att cct tta<br>Gln Asn Ile Lys Gly Asp Ala Ser Val Arg Lys Asn Lys Ile Pro Leu<br>145                    150                   155                  160 | 720 |
| cca cct cct cgg cct ctc ata aca ctt ccg aag aag tac caa ccc ttg<br>Pro Pro Pro Arg Pro Leu Ile Thr Leu Pro Lys Lys Tyr Gln Pro Leu<br>                    165                   170                  175 | 768 |
| ccc cct gag ccg gag agc agc agg cca cct tta tct cag aga cac acc<br>Pro Pro Glu Pro Glu Ser Ser Arg Pro Pro Leu Ser Gln Arg His Thr<br>          180                   185                   190 | 816 |
| ttt cca gaa gtc cag gga atg ccc agt cag ata agc tta agg gac tta<br>Phe Pro Glu Val Gln Gly Met Pro Ser Gln Ile Ser Leu Arg Asp Leu<br>                    195                   200                  205 | 864 |
| agt gag gtc ctt gaa gca gaa aaa gtt cct cat aac cag agg aag cct<br>Ser Glu Val Leu Glu Ala Glu Lys Val Pro His Asn Gln Arg Lys Pro<br>210                    215                   220 | 912 |
| gaa tca act cat ctg tta gaa aac caa aat act caa gag att cca ctt<br>Glu Ser Thr His Leu Leu Glu Asn Gln Asn Thr Gln Glu Ile Pro Leu<br>225                    230                   235                  240 | 960 |
| gcc att agc agt tct tca ttc acg aca agc aac cac agt gtg caa aac<br>Ala Ile Ser Ser Ser Ser Phe Thr Thr Ser Asn His Ser Val Gln Asn<br>                    245                   250                  255 | 1008 |
| aga gat cat aga gga ggc atg cag ccc tgt tct cct cag aga tgc cag<br>Arg Asp His Arg Gly Gly Met Gln Pro Cys Ser Pro Gln Arg Cys Gln<br>          260                   265                   270 | 1056 |
| cct cca gcc agc tgc agc cct cac gaa aat ata ctg ccc tat aaa tac<br>Pro Pro Ala Ser Cys Ser Pro His Glu Asn Ile Leu Pro Tyr Lys Tyr<br>                    275                   280                  285 | 1104 |
| aca agc tgg aga cca cct ttc ccc aaa agg tct gat aga aag gat gtc<br>Thr Ser Trp Arg Pro Pro Phe Pro Lys Arg Ser Asp Arg Lys Asp Val<br>          290                   295                   300 | 1152 |
| cag cac aat gaa tgg tac att gga gaa tac agc cgc cag gca gtg gaa<br>Gln His Asn Glu Trp Tyr Ile Gly Glu Tyr Ser Arg Gln Ala Val Glu<br>305                    310                   315                  320 | 1200 |
| gag gca ttc atg aag gag aac aag gat ggt agt ttc ttg gtc cga gat<br>Glu Ala Phe Met Lys Glu Asn Lys Asp Gly Ser Phe Leu Val Arg Asp<br>                    325                   330                  335 | 1248 |
| tgt tcc aca aaa tcc aag gaa gag ccc tat gtt ttg gct gtg ttt tat<br>Cys Ser Thr Lys Ser Lys Glu Glu Pro Tyr Val Leu Ala Val Phe Tyr<br>                    340                   345                  350 | 1296 |
| gag aac aaa gtc tac aat gta aaa atc cgc ttc ctg gag agg aat cag<br>Glu Asn Lys Val Tyr Asn Val Lys Ile Arg Phe Leu Glu Arg Asn Gln<br>          355                   360                   365 | 1344 |
| cag ttt gcc ctg ggg aca gga ctc aga gga gat gag aag ttt gat tca<br>Gln Phe Ala Leu Gly Thr Gly Leu Arg Gly Asp Glu Lys Phe Asp Ser | 1392 |

```
            370                 375                 380
gta gaa gac atc atc gaa cac tac aag aat ttt ccc att ata cta att     1440
Val Glu Asp Ile Ile Glu His Tyr Lys Asn Phe Pro Ile Ile Leu Ile
385                 390                 395                 400 gat ggg aaa gat aaa act ggg gtc cac agg aaa cag tgt cac ctc act     1488
Asp Gly Lys Asp Lys Thr Gly Val His Arg Lys Gln Cys His Leu Thr
                405                 410                 415 cag cca ctc cct ctc acc aga cac ctc ttg cct ctg tag cctggtcttt     1537
Gln Pro Leu Pro Leu Thr Arg His Leu Leu Pro Leu
                420                 425 gtgttatctt tggtttactg gattcagcgc ttccattgtt ttcattgatt tcaaaagttt    1597
attttctgtg ccttcaaggg acaacttttt taactttgga gaaagaaaaa acactctata    1657
acagagagtg gaaaatcact cacggttttg aaagttcaaa ccacagagaa aatatttata    1717
acatgcaaaa aataaaaaca tttctagtaa ctggccactg gaaataaat aaaaataaaa     1777 actaaaaaaa aagaaaaaaa aaaaaaaaaa aaaaaaa                             1814

<210> SEQ ID NO 4
<211> LENGTH: 428
<212> TYPE: PRT
<213> ORGANISM: Homo sapiens

<400> SEQUENCE: 4

Met Asn Arg Gln Gly Asn Arg Lys Thr Thr Lys Glu Gly Ser Asn Asp
1               5                   10                  15

Leu Lys Phe Gln Asn Phe Ser Leu Pro Lys Asn Arg Ser Trp Pro Arg
            20                  25                  30

Ile Asn Ser Ala Thr Gly Gln Tyr Gln Arg Met Asn Lys Pro Leu Leu
        35                  40                  45

Asp Trp Glu Arg Asn Phe Ala Ala Val Leu Asp Gly Ala Lys Gly His
    50                  55                  60

Ser Asp Asp Tyr Asp Pro Glu Leu Arg Met Glu Glu Thr Trp
65                  70                  75                  80

Gln Ser Ile Lys Ile Leu Pro Ala Arg Pro Ile Lys Glu Ser Glu Tyr
                85                  90                  95

Ala Asp Thr His Tyr Phe Lys Val Ala Met Asp Thr Pro Leu Pro Leu
            100                 105                 110

Asp Thr Arg Thr Ser Ile Ser Ile Gly Gln Pro Thr Trp Asn Thr Gln
        115                 120                 125

Thr Arg Leu Glu Arg Val Asp Lys Pro Ile Ser Arg Asp Val Arg Ser
    130                 135                 140

Gln Asn Ile Lys Gly Asp Ala Ser Val Arg Lys Asn Lys Ile Pro Leu
145                 150                 155                 160

Pro Pro Pro Arg Pro Leu Ile Thr Leu Pro Lys Lys Tyr Gln Pro Leu
                165                 170                 175

Pro Pro Glu Pro Glu Ser Ser Arg Pro Pro Leu Ser Gln Arg His Thr
            180                 185                 190

Phe Pro Glu Val Gln Gly Met Pro Ser Gln Ile Ser Leu Arg Asp Leu
        195                 200                 205

Ser Glu Val Leu Glu Ala Glu Lys Val Pro His Asn Gln Arg Lys Pro
    210                 215                 220

Glu Ser Thr His Leu Leu Glu Asn Gln Asn Thr Gln Glu Ile Pro Leu
225                 230                 235                 240

Ala Ile Ser Ser Ser Phe Thr Ser Asn His Ser Val Gln Asn
                245                 250                 255
```

-continued

```
Arg Asp His Arg Gly Gly Met Gln Pro Cys Ser Pro Gln Arg Cys Gln
            260                 265                 270

Pro Pro Ala Ser Cys Ser Pro His Glu Asn Ile Leu Pro Tyr Lys Tyr
            275                 280                 285

Thr Ser Trp Arg Pro Pro Phe Pro Lys Arg Ser Asp Arg Lys Asp Val
    290                 295                 300

Gln His Asn Glu Trp Tyr Ile Gly Glu Tyr Ser Arg Gln Ala Val Glu
305                 310                 315                 320

Glu Ala Phe Met Lys Glu Asn Lys Asp Gly Ser Phe Leu Val Arg Asp
                325                 330                 335

Cys Ser Thr Lys Ser Lys Glu Glu Pro Tyr Val Leu Ala Val Phe Tyr
            340                 345                 350

Glu Asn Lys Val Tyr Asn Val Lys Ile Arg Phe Leu Glu Arg Asn Gln
            355                 360                 365

Gln Phe Ala Leu Gly Thr Gly Leu Arg Gly Asp Glu Lys Phe Asp Ser
    370                 375                 380

Val Glu Asp Ile Ile Glu His Tyr Lys Asn Phe Pro Ile Ile Leu Ile
385                 390                 395                 400

Asp Gly Lys Asp Lys Thr Gly Val His Arg Lys Gln Cys His Leu Thr
                405                 410                 415

Gln Pro Leu Pro Leu Thr Arg His Leu Leu Pro Leu
            420                 425
```